United States Patent [19]

Knowles et al.

[11] Patent Number: 5,565,147
[45] Date of Patent: Oct. 15, 1996

[54] PHOTOCHROMIC NAPHTHOPYRAN COMPOUNDS

[75] Inventors: David B. Knowles, Apollo; Barry Van Gemert, Murrysville, both of Pa.

[73] Assignee: Transitions Optical, Inc., Pinellas Park, Fla.

[21] Appl. No.: 459,432

[22] Filed: Jun. 2, 1995

Related U.S. Application Data

[62] Division of Ser. No. 225,022, Apr. 8, 1994, Pat. No. 5,451,344.

[51] Int. Cl.$^6$ .......................... G02B 5/23; C07D 405/10; C07D 407/10; C08K 5/15
[52] U.S. Cl. .......................... 252/586; 549/384; 549/277; 546/62; 524/110; 524/99
[58] Field of Search .................................. 549/384, 277; 546/62; 524/110, 99; 252/586

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,816,584 | 3/1988 | Kwak et al. | 544/71 |
| 4,818,096 | 4/1988 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/160 |
| 5,066,818 | 11/1991 | Van Gemert | 549/389 |
| 5,238,981 | 8/1993 | Knowles | 524/110 |
| 5,274,132 | 12/1993 | Van Gemert | 549/389 |

FOREIGN PATENT DOCUMENTS 62-195383  6/1987  Japan.

OTHER PUBLICATIONS

*Friedel–Crafts and Related Reactions*, George A. Olah, Interscience Publishers, vol. 3, Chap. XXXI, pp. 1–8, 1964.
*Advances in Heterocyclic Chemistry*, A. R. Katritzky and A. J. Boulton, Academic Press, vol. 18, pp. 361–371, 1975.
*Organic Reactions*, Krieger Publishing Co., vol. II, Chapter 1, pp. 1–48. Reprint edition 1981.
*Organic Synthesis*, John Wiley and Sons, Inc., vol. 49, pp. 90–93, 1969.
*Chromenes, Chromanones, and Chromones*, G. P. Ellis, John Wiley and Sons, Chapter II, pp. 43–70, 1977.
*Organic Reactions*, John Wiley and Sons, Inc., vol. VII, Chapter 1, pp. 1–58, 1953.

*Primary Examiner*—Nicky Chan
*Attorney, Agent, or Firm*—Frank P. Mallak; Irwin M. Stein

[57] ABSTRACT

Described are novel reversible photochromic diaryl-3H-naphtho[2,1-b]pyran compounds having a substituted or unsubstituted, five or six member heterocyclic ring fused to the g, i, or l side of the naphthopyran. The heterocyclic ring contains an oxygen or nitrogen atom and is attached to the number 5, 6, 7, 8, 9, or 10 carbon atom of the naphtho portion of the naphthopyran. Also described are organic host materials containing such compounds. Articles such as ophthalmic lenses or other plastic transparencies that incorporate the novel naphthopyran compounds or combinations thereof with complementary photochromic compounds, e.g., spiro(indoline)oxazine-type compounds, are also described.

22 Claims, No Drawings

PHOTOCHROMIC NAPHTHOPYRAN COMPOUNDS

This is a division of application Ser. No. 08/225,022, filed Apr. 8, 1994 now U.S. Pat. No. 5,451,344.

The present invention relates to certain novel naphthopyran compounds. More particularly, this invention relates to novel photochromic naphthopyran compounds and to compositions and articles containing such novel naphthopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of these compounds with visible light or upon raising the temperature to above about 0° C. is reported to reverse the coloration to a colorless state.

The present invention relates to novel naphthopyran compounds which have fused to the g, i, or l side of the naphthopyran a substituted or unsubstituted, five or six member heterocyclic ring containing an oxygen or nitrogen atom. The heterocyclic ring is fused so that the oxygen or nitrogen atom is directly attached to the number 5, 6, 7, 8, 9, or 10 carbon atom of the naphtho portion of the naphthopyran. These compounds have demonstrated a dramatic bathochromic shift in the ultraviolet and visible spectra resulting in higher sensitivity levels than corresponding compounds having no substituents on the naphtho portion of the naphthopyran or an acyclic oxy-bearing substituent at the number 8 carbon atom as described in U.S. Pat. No. 5,238,981.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

A naphthopyran such as 3,3-diphenyl-3H-naphtho[2,1-b] pyran changes color on exposure to ultraviolet light; but, at room temperature and above, it's sensitivity is low, i.e., on exposure to ultraviolet light, it's optical density changes too slowly, and it's optical density at saturation is too low for use in optical applications. Another naphthopyran, 3,3-diphenyl-8-methoxy-3H-naphtho[2,1-b]pyran, described in U.S. Pat. No. 5,238,981, has improved properties for optical applications as compared to the aforedescribed compound and corresponding compounds having a methoxy substituent at the number 5, 7, or 9 carbon atoms. These improvements in properties, i.e., enhanced sensitivity and optical density at saturation, are due in large part to the compound's lambda max (UV), i.e., the maximum wavelength in the ultraviolet range closest to the visible spectrum, being shifted towards the near visible threshold range, which is from about 390 to 410 nanometers. Nevertheless, further improvements in sensitivity and optical density at saturation are desirable and have been pursued.

In accordance with the present invention, there have been discovered certain novel diaryl-3H-naphtho[2,1-b]pyrans which have a substituted or unsubstituted, five or six member oxygen or nitrogen-containing heterocyclic ring fused to the g, i, or l side of the naphthopyran. The oxygen or nitrogen atom in the fused heterocyclic ring is directly attached to the number 5, 6, 7, 8, 9, or 10 carbon atom of the naphtho portion of the naphthopyran. The naphthopyrans of the present invention exhibit a dramatic bathochromic shift of their absorption maxima in both the UV spectrum of the unactivated form and the visible spectrum of the activated form. The shift in the ultraviolet spectrum results in the compounds of the present invention having a lambda max (UV) much closer to and in many cases within the near visible threshold range and increased sensitivity, vis-a-vis, the photochromic naphthopyrans of the '981 patent. A further benefit of the bathochromic shift of the absorption maxima in the ultraviolet spectrum is demonstrated by the more uniform performance of the compounds when used in optical applications. Photochromic ophthalmic lenses rely on the UV component of sunlight for activation. The intensity of solar UV at different wavelengths can vary because the shorter UV wavelengths are attenuated by the earth's atmosphere. Early or late in the day, at high latitudes, and in non-summer months, this attenuation is even more pronounced due to the greater distance the sun's rays have to pass through the atmosphere. The shift in the visible spectrum results in the activated naphthopyran compounds of the present invention being more orange than yellow in color, which allows their use in combination with blue photochromic organic compounds to form a neutral gray photochromic article, e.g., and ophthalmic lens, as described hereinafter.

The naphthopyran compounds of the present invention have a high quantum efficiency for coloring, a good sensitivity and saturated optical density, and an acceptable bleach or fade rate. Such compounds are particularly suitable for use in ophthalmic applications. These compounds may be represented by the following graphic formulae IA1, IA2, and IA3 in which the letters a through n represent the sides of the naphthopyran rings, and the numbers represent the numbering of the ring atoms of the naphthopyrans:

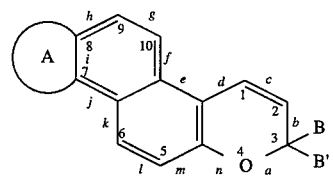

IA1

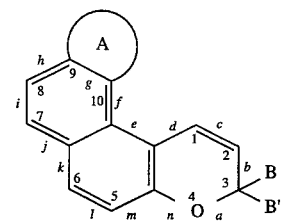

IA2

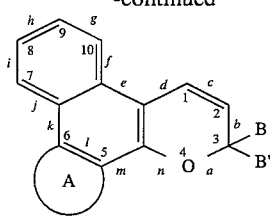

IA3

In graphic formulae IA1, IA2, and IA3, the group represented by A is a substituted or unsubstituted, five or six member heterocyclic ring fused to the g, i, or l side of the naphthopyran and is represented by the following graphic formulae IIA through IIF:

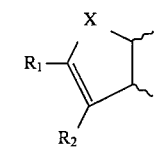

IIA

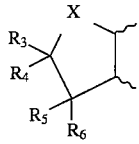

IIB

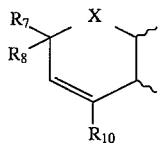

IIC

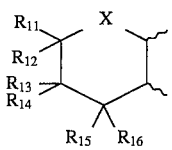

IID

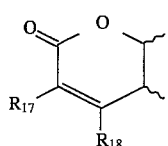

IIE

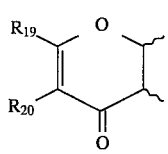

IIF

In graphic formulae IIA through IID, X may be an oxygen or a nitrogen atom, said nitrogen atom being substituted with hydrogen or a $C_1-C_4$ alkyl. $R_1$ may be hydrogen, $C_1-C_6$ alkyl, substituted or unsubstituted phenyl, carboxy, or $C_1-C_6$ alkoxycarbonyl. Preferably, $R_1$ is hydrogen, $C_1-C_3$ alkyl, substituted or unsubstituted phenyl, carboxy, or $C_1-C_3$ alkoxycarbonyl. $R_2$ may be hydrogen, $C_1-C_6$ alkyl, or substituted or unsubstituted phenyl. Preferably, $R_2$ is hydrogen, $C_1-C_3$ alkyl, or substituted or unsubstituted phenyl. $R_3$, and $R_4$ may each be hydrogen, $C_1-C_6$ alkyl, or phenyl. Preferably, $R_3$ and $R_4$ are each hydrogen, $C_1-C_3$ alkyl, or phenyl. $R_5$ and $R_6$ may be each hydrogen, $C_1-C_6$ alkyl, phenyl, hydroxy, $C_1-C_6$ alkoxy, or acetoxy. Preferably, $R_5$ and $R_6$ are each hydrogen, $C_1-C_3$ alkyl, phenyl, hydroxy, $C_1-C_3$ alkoxy, or acetoxy. $R_7$, $R_8$, and $R_{10}$ may each be hydrogen, $C_1-C_6$ alkyl, or phenyl, provided that when $R_7$ is phenyl, $R_8$ is hydrogen or $C_1-C_6$ alkyl and when $R_8$ is phenyl, $R_7$ is hydrogen or $C_1-C_6$ alkyl. Preferably, $R_7$, $R_8$, and $R_{10}$ are each hydrogen, $C_1-C_3$ alkyl, or phenyl. Most preferably, $R_1$, $R_2$, $R_3$, $R_4$, $R_5$, $R_6$, $R_7$, $R_8$, and $R_{10}$ are each hydrogen or methyl. $R_{11}$, $R_{12}$, $R_{13}$, $R_{14}$, $R_{15}$, and $R_{16}$ may each be hydrogen, $C_1-C_6$ alkyl, $C_1-C_6$ alkoxy, or phenyl. Preferably, $R_{11}$, $R_{12}$, $R_{13}$, $R_{14}$, $R_{15}$, and $R_{16}$ are each hydrogen, $C_1-C_3$ alkyl, $C_1-C_3$ alkoxy, or phenyl. Most preferably, $R_{11}$, $R_{12}$, $R_{13}$, $R_{14}$, $R_{15}$, and $R_{16}$ are each hydrogen, methyl, or methoxy.

In graphic formulae IIE and IIF, $R_{17}$ may be hydrogen, $C_1-C_6$ alkyl, substituted or unsubstituted phenyl, or halogen. Preferably, $R_{17}$ is hydrogen, $C_1-C_3$ alkyl, substituted or unsubstituted phenyl, or halogen. Most preferably, $R_{17}$ is hydrogen, methyl, or chloro. $R_{18}$ may be hydrogen, $C_1-C_6$ alkyl, phenyl, carboxy, $C_1-C_6$ alkoxycarbonyl, or $C_1-C_6$ haloalkoxycarbonyl. Preferably, $R_{18}$ is hydrogen, $C_1-C_3$ alkyl, phenyl, carboxy, $C_1-C_3$ alkoxycarbonyl, or $C_1-C_3$ haloalkoxycarbonyl. $R_{19}$ and $R_{20}$ may each be hydrogen, $C_1-C_6$ alkyl, or phenyl. Preferably, $R_{19}$ and $R_{20}$ are each hydrogen, $C_1-C_3$ alkyl, or phenyl. Most preferably, $R_{18}$, $R_{19}$, and $R_{20}$ are each hydrogen or methyl. In $R_1-R_{20}$, the phenyl substituents may be $C_1-C_5$ alkyl and the halogen or (halo) groups may be chloro or bromo.

In graphic formulae IA1, IA2, and IA3, B and B' may each be selected from the group consisting of (i) the substituted or unsubstituted aryl groups phenyl and naphthyl; (ii) the substituted or unsubstituted heterocyclic aromatic groups pyridyl, furyl, benzofuryl, thienyl, and benzothienyl; and (iii) B and B' taken together form the adamantyl group. The aryl and heterocyclic substituents of B and B' may each be selected from the group consisting of hydroxy, $C_1-C_5$ alkyl, $C_1-C_5$ haloalkyl, which includes mono-, di-, and trihalo substituents, $C_1-C_5$ alkoxy, $C_1-C_5$ alkoxy($C_1-C_4$)alkyl, $C_1-C_5$ dialkylamino, acryloxy, methacryloxy, and halogen, said halogen or (halo) groups being fluoro, chloro, or bromo.

Preferably, B and B' are represented respectively by the following graphic formulae:

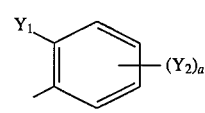

IIIA

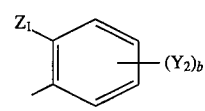

IIIB

In graphic formulae IIIA and IIIB, $Y_1$ and $Z_1$ may each be selected from the group consisting of hydrogen, $C_1-C_5$ alkyl, $C_1-C_5$ alkoxy, fluoro, and chloro; $Y_2$ and $Z_2$ are each selected from the group consisting of $C_1-C_5$ alkyl, $C_1-C_5$ alkoxy, hydroxy, halogen, e.g., chloro, fluoro, and bromo, acryloxy, and methacryloxy, and a and b are each integers from 0 to 2. Most preferably, $Y_1$ and $Z_1$ are each hydrogen, $C_1-C_3$ alkyl, $C_1-C_3$ alkoxy, or fluoro, $Y_2$ and $Z_2$ are each $C_1-C_3$ alkyl or $C_1-C_3$ alkoxy, a is the integer 0 or 1, and b is an integer from 0 to 2.

The preferred naphthopyrans of the present invention are represented in the following graphic formula IB. In graphic formula IB, the A group represents formulae IIA through IID with X being an oxygen atom, formulae IIE and IIF. The A group is fused so that the oxygen atom of formulae IIA through IIF is attached to the number 8 carbon atom of the naphtho portion of the naphthopyran.

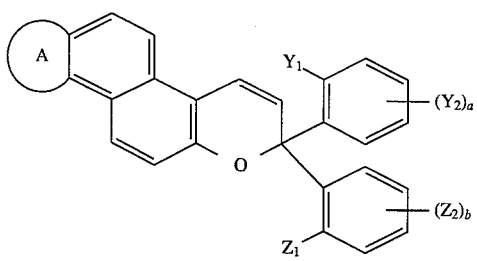

IB

Compounds represented by graphic formula IB are prepared by coupling the appropriate five or six member heterocyclic ring fused naphthol by methods described hereinafter with the appropriate substituted propargyl alcohol as shown in Reaction H. The propargyl alcohol represented by graphic formula VII, which is used in Reaction H, may be prepared by methods described in Reaction A and Reaction B. Compounds represented by graphic formula VI may be purchased from fine chemical manufacturers or may be prepared by Friedel-Crafts methods as shown in Reaction A. See the publication, Friedel-Crafts and Related Reactions, George A. Olah, Interscience Publishers, 1964, Vol. 3, Chapter XXXI (Aromatic Ketone Synthesis).

In Reaction A, the appropriately substituted or unsubstituted benzoyl chloride of graphic formula V and a commercially available substituted benzene compound of graphic formula IV are dissolved in a solvent, such as carbon disulfide or methylene chloride, and reacted in the presence of a Lewis acid, such as aluminum chloride, to form the corresponding substituted benzophenone represented by graphic formula VI.

REACTION A

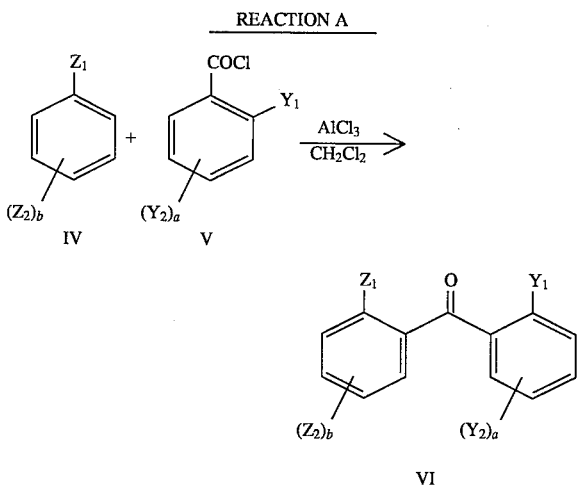

In Reaction B, the substituted benzophenone represented by graphic formula VI is reacted with sodium acetylide in a suitable solvent, such as dry tetrahydrofuran (THF), to form the corresponding propargyl alcohol, which may be represented by graphic formula VII.

REACTION B

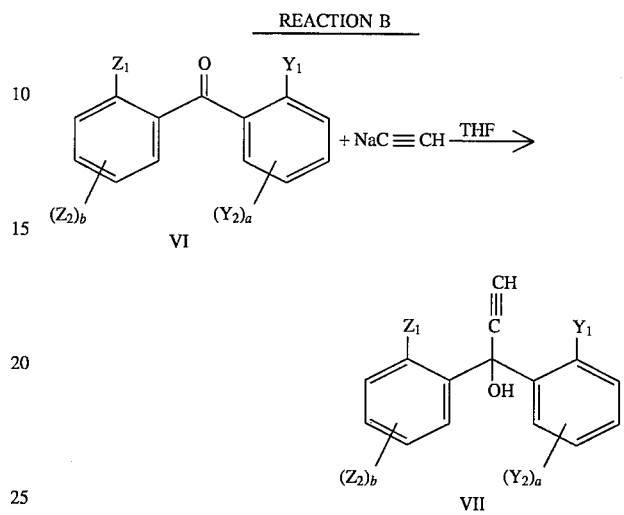

In Reaction C, 6-bromo-2-naphthol and chloroacetone, represented by graphic formulae VIII and IX, respectively, are dissolved in reagent grade acetone containing anhydrous potassium carbonate and refluxed to produce the naphthyloxyacetone of graphic formula X. Cyclodehydration of naphthyloxyacetone under low temperatures in concentrated sulfuric acid yields 7-bromo-1-methylnaphtho[2,1-b]furan represented by graphic formula XI. Further examples of this reaction may be found in *Advances in Heterocyclic Chemistry* Vol.18, pages 361–371, 1975. Solvolysis of the 7-bromo-1-methylnaphtho[2,1-b]furan to 7-hydroxy-1-methylnaphtho[2,1-b]furan represented by graphic formula XII takes place under high pressure and elevated temperature using copper bronze as the catalyst. Other substituted 7-hydroxynaphtho[2,1-b]furans may be synthesized by replacing chloroacetone (IX) with other reactants such as 3-chloro-2-butanone or 1-bromo-2-butanone. Coupling the resulting 7-hydroxynaphtho[2,1-b]furan, compound XII, with the appropriate propargyl alcohol would result in a compound represented by graphic formula IB having formula IIA as group A.

REACTION C

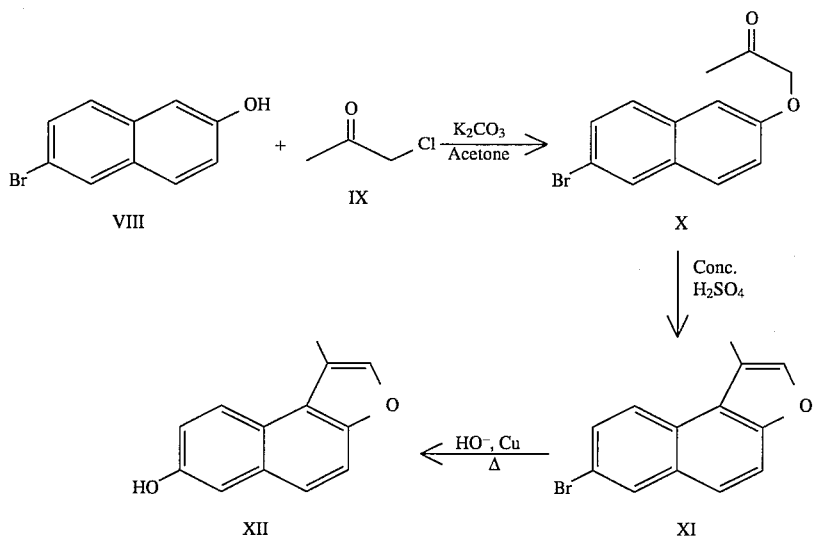

In reaction D, 6-bromo-2-naphthol and allylbromide, represented by the graphic formulae VIII and XIII, respectively, are refluxed together in ethanoic potassium hydroxide to produce 2-allyloxy-6-bromonaphthalene of graphic formula XIV. 2-Allyloxy-6-bromonaphthalene undergoes a Claisen rearrangement under high temperatures followed by acid catalyzed ring closure to produce 7-bromo-1,2-dihydro-2-methylnaphtho[2,1-b]furan of graphic formula XV. See *Organic Reaction* Vol. II, 1944, pages 1 to 48. The conversion of 7-bromo-1,2-dihydro-2-methylnaphtho[2,1-b]furan to 7-hydroxy-1,2-dihydro-2-methylnaphtho[2,1-b]furan represented by graphic formuale XVI is accomplished thru a series of steps described in *Organic Synthesis* Vol.49 pages 90–93, 1972. Other substituted 7-hydroxy-1,2-dihydronaphtho[2,1-b]furans may be synthesized by replacing allylbromide (XIII) with another reactant such as 3-bromo-2-methyl-propene. Coupling the resulting 7-hydroxy-1,2-dihydronaphtho[2,1-b]furan with the appropriate propargyl alcohol would result in compounds represented by graphic formula IB having formula IIB as group A.

In Reaction E, 6-bromo-2-naphthol and propargyl bromide represented by graphic formulae VIII and XVII, respectively, are refluxed together in ethanoic potassium hydroxide. The resulting propargyl naphthyl ether represented by graphic formula XVIII will, when refluxed in N,N-dimethylaniline (DMA), yield 8-bromo-3H-naphtho[2,1-b]pyran represented by graphic formula XIX. See *Chromenes, Chromanones and Chromones* Chapter II, E. E. Schweizer and D. Meeder-Nycz, 1977, pages 43 to 70. The conversion of 8-bromo-3H-naphtho[2,1-b]pyran to 8-hydroxy-3H-naphtho[2,1-b]pyran of graphic formula XX proceeds thru a series of steps described in *Organic Synthesis* Vol. 49 pages 90–93, 1972. Other substituted 8-hydroxy-3H-naphtho[2,1-b]pyrans may be synthesized by replacing propargyl bromide with another reactant such as substituted 3-bromo-1-alkynes. Coupling the resulting 8-hydroxy-3H-naphtho[2,1-b]pyran with the appropriate propargyl alcohol would result in compounds represented by graphic formula IB having formula IIC as group A.

REACTION D

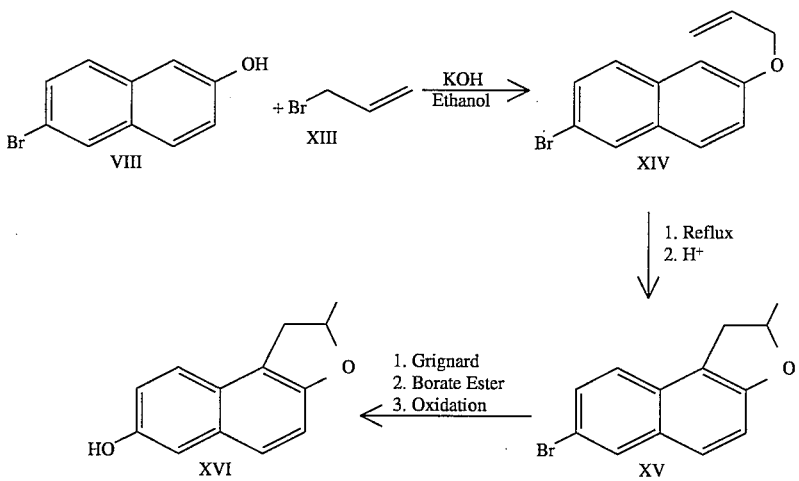

REACTION E

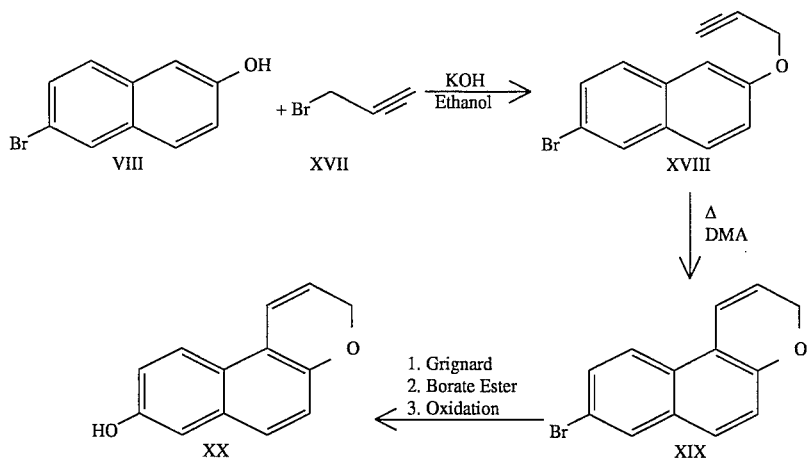

In Reaction F, 6-bromo-2-naphthol and 1-bromo-3-chloropropane represented by graphic formulae VIII and XXI, respectively, are refluxed together in methanoic potassium hydroxide to form a haloalkyl naphthyl ether represented by graphic formula XXII. Ring closure is achieved by Friedel Crafts methods and yields 8-bromo-1,2-dihydro-3H-naphtho[2,1-b]pyran represented by graphic formula XXIII. Solvolysis of 8-bromo-1,2-dihydro-3H-naphtho[2,1-b]pyran to 1,2-dihydro-8-hydroxy-3H-naphtho[2,1-b]pyran represented by graphic formula XXIV takes place under high pressure and elevated temperature using copper bronze as the catalyst. Other substituted 1,2-dihydro-8-hydroxy-3H-naphtho[2,1-b]pyrans may be synthesized by replacing 1-bromo-3-chloropropane with another reactant such as 1-bromo-3-chlorobutane. Coupling the resulting 1,2-dihydro-8-hydroxy-3H-naphtho[2,1-b]pyran with the appropriate propargyl alcohol would result in compounds represented by graphic formula IB having formula IID as group A.

In Reaction G, 2,6-dihydroxynaphthalene and ethylacetoacetate represented by graphic formulae XXV and XXVI, respectively, are condensed using aqueous sulfuric acid under low temperature to yield both 8-hydroxy-1-methyl-3H-naphtho[2,1-b]pyran-3-one (XXVII) and 8-hydroxy-3-methyl-1H-naphtho[2,1-b]pyran-1-one (XXVIII). Other potential substituents which may be used in place of XXVI are discussed in *Organic Reactions* Vol. VII, Chapter 1, pages 1–58, 1953. Coupling the resulting 8-hydroxy-1-methyl-3H-naphtho[2,1-b]pyran-3-one and 8-hydroxy-3-methyl-1H-naphtho[2,1-b]pyran-1-one with the appropriate propargyl alcohol would result in compounds represented by graphic formula IB having formulae IIE or IIF, respectively, as group A.

REACTION F

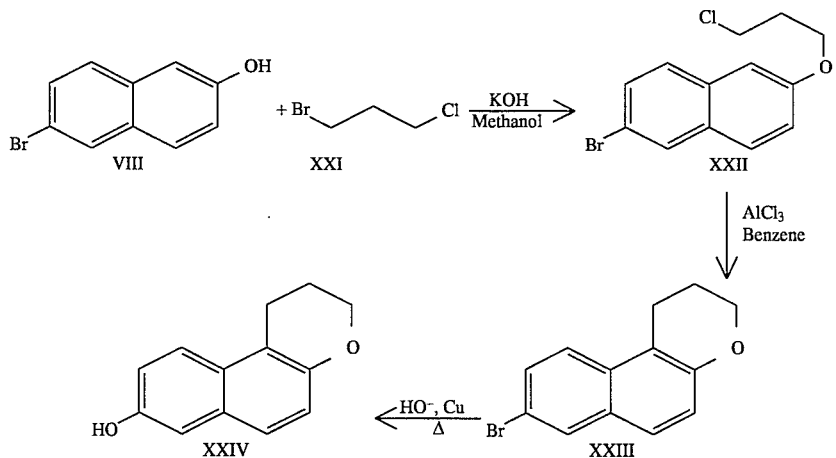

REACTION G

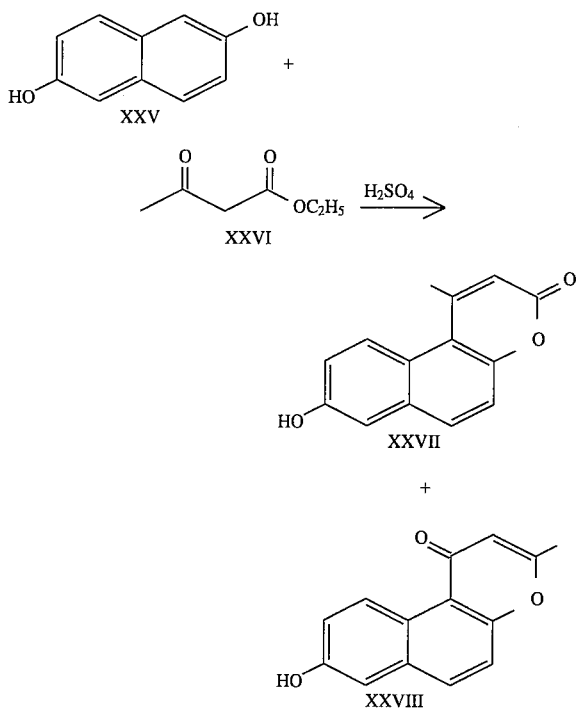

In Reaction H, the heterocyclic hydroxynaphthalenes described herein, e.g., compounds XII, XVI, XX, XXIV, XXVII, or XXVIII, may be represented by graphic formulae XXIX. Compound XXIX may be coupled with the propargyl alcohol represented by graphic formula VII to produce compounds represented by graphic formula IB.

REACTION H

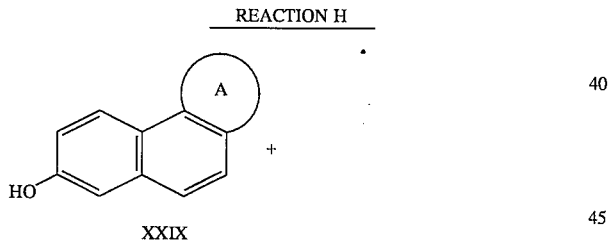

-continued
REACTION H

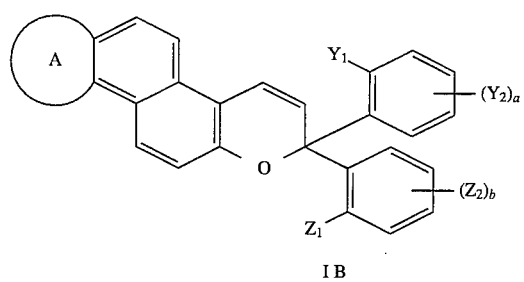

Compounds represented by graphic formulae IA2 and IA3, having A fused to the g or l side of the naphthopyran, may be prepared by coupling an appropriate propargyl alcohol with one of the isomeric naphthols represented by the following graphic formulae XXX and XXXI:

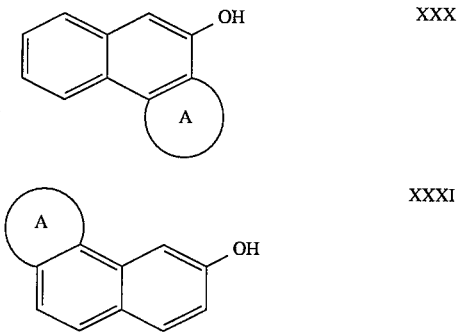

The isomeric naphthols represented by graphic formulae XXX and XXXI may be prepared by using synthetic strategies analogous to those presented in Reactions C thru G. Appropriate starting materials which are commercially available include 2,3-dihydroxynaphthalene, 1,3-dihydroxynaphthalene, and 2,7-dihydroxynaphthalene. Other dihydroxynaphthalenes, that are not readily available, may be prepared from the appropriately substituted naphthalene-sulfonic acid by heating with alkali at 230° C. or by other methods reported in the literature.

Compounds represented by graphic formula IB having nitrogen as X in the fused heterocyclic ring represented by graphic formula II A may be prepared from intermediates produced according to the reactions described in Reaction J. Thus, the naphthol represented by graphic formula VIII may be converted by the Bucherer reaction to the aminonaphthalene represented by graphic formula XXXII. The aminonaphthalene may undergo the Bischler indole synthesis reaction to yield the compound of graphic formula XXXIII. The alkylation of compound XXXIII to produce compound XXXIV may be accomplished using alkylating agents that include $C_1$–$C_4$ alkyltosylates, $C_1$–$C_4$ alkyliodides, and $C_1$–$C_4$ alkylbromides. The R group of compound XXXIV may be a $C_1$–$C_4$ alkyl. The compound represented by graphic formula XXXIV may be converted to the compound represented by graphic formula XXXV by a series of steps described in *Organic Synthesis* Vol. 49 pages 90–93, 1972. similar synthetic strategies may be used to prepare naphthols having other nitrogen containing heterocyclics fused to the g, i, or l sides.

REACTION J

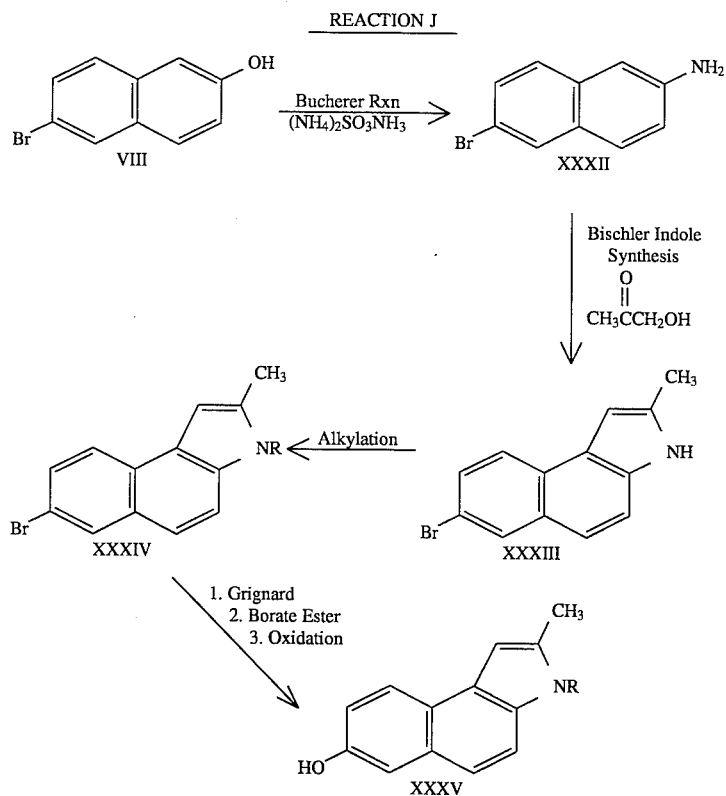

Compounds represented by graphic formulae IA1, IA2, and IA3, e.g., graphic formula IB, may be used in those applications in which organic photochromic substances may be employed, such as optical lenses, e.g., plano and vision correcting ophthalmic lenses, face shields, goggles, visors, camera lenses, windows, automotive windshields, aircraft and automotive transparencies, e.g., T-roofs, sidelights, and backlights, plastic films and sheets, textiles, and coatings, e.g., coating compositions such as paints and verification marks on security documents, e.g., documents such as banknotes, passports, and drivers' licenses for which authentication or verification of authenticity may be desired. Naphthopyrans represented by graphic formulae IA1 through IA3 exhibit color changes from colorless to colors ranging from yellow to orange/red.

Examples of contemplated naphthopyrans within the scope of the invention are the following:

(a) 7-(phenyl)-7-(3-methylphenyl)-7H-2-methyl -2,3-dihydrofuro[3',2',:5,6]naphtho[2,1-b]pyran;
(b) 7,7-diphenyl-7H-2-methyl-2,3-dihydrofuro[3',2',:5,6]naphtho[2,1-b]pyran;
(c) 7-(phenyl)-7-(3-trifluoromethylphenyl)-7H-2-methyl-2,3-dihydrofuro[3',2',:5,6]naphtho[2,1-b]pyran;
(d) 7-(phenyl)-7-(3-fluorophenyl)-7H-2-methyl-2,3-dihydrofuro[3',2',:5,6]naphtho[2,1-b]pyran;
(e) 7-(phenyl)-7-(3-methoxyphenyl)-7H-2-methyl- 2,3-dihydrofuro[3',2',:5,6]naphtho[2,1-b]pyran;
(f) 7-(2-fluorophenyl)-7-(4-methoxyphenyl)-7H-2-methyl-2,3-dihydrofuro[3',2',:5,6]naphtho[2,1-b]pyran;
(g) 7,7-diphenyl-7H-3-methylfuro[3',2',:5,6]naphtho[2,1-b]pyran;
(h) 9,9-diphenyl-3H-9H-1,2-dihydronaphtho[2,1-b:6,5-b']dipyran;
(i) 9-(2,4-dimethoxyphenyl)-9-(4'-methoxyphenyl)-1-methyl-3H,9H-naphtho[2,1-b:6,5-b']dipyran-3-one; and
(j) 9-(2,4-dimethoxyphenyl)-9-(4'-methoxyphenyl)-3-methyl-1H,9H-naphtho[2,1-b:6,5-b']dipyran-1-one.

Commercially available photoreactive inorganic glass lenses containing silver halide particles darken to a neutral gray or brown color in sunlight. In order to duplicate this color change in a plastic lens using the organic photochromic naphthopyrans of the present invention, it is contemplated that such naphthopyrans be used in combination with other appropriate complementary organic photochromic materials so that together they produce the desired gray or brown color shade when the plastic lens containing such photochromic materials is exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue color compound.

A first group of organic photochromic compounds contemplated for use as complementary photochromic materials are those having an activated absorption maximum within the visible range of greater than 590 nanometers, e.g., between about greater than 590 to about 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. No. Nos. 3,562,172; 3,578,602; 4,215,010; and 4,342,668. Spiro(indoline)naphthoxazines having certain substituents on the 8' and 9' positions of the naphthoxazine portion of the molecule, such as 1,3,3-trimethyl-5-methoxy-9'-methoxycarbonyl-8'-acetoxy-spiro[indoline-2,3'-[3H] naphth[2,1-b][1,4]oxazine], are the subject of U.S. patent application Ser. No. 07/993,587, filed Dec. 21, 1992, now U.S. Pat. No. 5,405,958. Spiro(indoline)pyridobenzoxazines are described in U.S. Pat. No. 4,637,698. Spiro(benzindoline)pyridobenzoxazines and spiro(benzindoline)naphthoxazines are described in U.S. Pat. No. 4,931,219. Spiro(benzindoline)naphthopyrans are described in Japanese Patent Publication 62/195383. Spiro(indoline)benzoxazines are described in U.S. Pat. No. 4,816,584. Spiro(indoline)benzopyrans, spiro(indoline)naphthopyrans and spiro(indoline)quinopyrans are described, for example, in U.S. Pat. No. 4,880,667. Benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of organic photochromic substances contemplated for use as complementary photochromic compounds are those having at least one absorption maximum and preferably two absorption maxima, within the visible range of between about 400 and less than 550 nanometers. These materials typically exhibit a yellow to red/purple color when exposed to ultraviolet light in an appropriate solvent or matrix. Such compounds include certain chromenes, i.e., benzopyrans and 3H-naphtho[2,1-b]pyrans, many of which are described in the open literature, e.g., U.S. Pat. Nos. 3,567,605; 4,826,977; and 5,066,818. Examples of benzopyrans and naphthopyrans having a spiroadamantane group in the 2-position of the ring are described in U.S. Pat. No. 4,826,977. Naphthopyrans, i.e., 3H-naphtho[2,1-b]pyrans, having at least one ortho-substituted phenyl substituent at the 3-position of the pyran ring are described in U.S. Pat. No. 5,066,818. Naphthopyran compounds having certain substituents at the number 8 carbon atom and certain substituents at the number 7 or 9 carbon atom, all substituents being on the naphtho portion of the naphthopyran, are the subject of U.S. patent application Ser. No. 08/080,246, filed Jun. 21, 1993 now U.S. Pat. No. 5,466,398. Naphthopyrans substituted at the 3 position of the pyran ring with (i) an aryl substituent and (ii) a phenyl substituent having a five or six member heterocyclic ring fused at the number 3 and 4 carbon atoms of the phenyl substituent are the subject of U.S. patent application Ser. No. 08/080,250 filed Jun. 21, 1993, now U.S. Pat. No. 5,384,077 Naphthopyran compounds substituted at the number 8 carbon atom on the naphtho portion of the naphthopyran ring, with for example, a methoxy group are the subject of U.S. Pat. No. 5,238,931. Naphthopyran compounds, examples of which are 3-aryl-3-arylalkenyl naphthopyrans, are the subject of U.S. patent application Ser. No. 07/954,630, filed Sep. 30, 1992, now U.S. Pat. No. 5,274,132. Naphthopyran compounds having certain substituents at the number 5 and 6 carbon atoms of the naphtho portion of the naphthopyran and at the 2-position of the pyran ring are the subject of U.S. patent application Ser. No. 08/164,187, filed Dec. 9, 1993 now U.S. Pat. No. 5,458,814.

A third group of organic photochromic substances contemplated for use as complementary photochromic compounds are those having an absorption maximum within the visible range of between about 400 to about 500 nanometers and another absorption maximum within the visible range of between about 500 to about 700 nanometers. These materials typically exhibit color(s) ranging from yellow/brown to purple/gray when exposed to ultraviolet light in an appropriate solvent or matrix. Examples of these compounds include certain benzopyran compounds, such as those having substituents at the 2-position of the pyran ring and a substituted or unsubstituted heterocyclic ring, such as a benzothieno or benzofurano ring fused to the benz portion of the benzopyran. Such materials are the subject of U.S. patent application Ser. No. 08/220,344, filed Mar. 30, 1994, now U.S. Pat. No. 5,429,774.

The disclosures of such photochromic compounds in the aforedescribed patents and patent applications are incorporated herein, in toto, by reference. Photochromic articles containing a naphthopyran(s) of the present invention may also contain one of the aforesaid complementary photochromic compounds or a mixture of such photochromic compounds, as desired. Mixtures of photochromic compounds may be used to attain certain activated colors such as a near neutral gray or brown.

The novel naphthopyran compounds of the present invention may be described as photochromic compounds that exhibit activated colors of from yellow to orange/red, and therefore may be used in place of or in combination with the aforesaid second group of photochromic compounds. The compounds of the present invention (hereinafter referred to as a second group photochromic compound) may be combined with or used in conjunction with the first group of photochromic compounds that color to purple/blue, e.g., the spirooxazine-type compounds, or with other photochromic substances in the aforesaid second group of photochromic compounds. Either members of the first or second group of photochromic compounds or mixtures of such compounds may be combined with or used in conjunction with the third group of described organic photochromic compounds that color from yellow/brown to purple/gray provided that the compounds of the first and second groups are different than the third group. Each of the photochromic compounds or substances containing same described herein may be used in amounts and in a ratio such that an organic host material to which the mixture of compounds is applied or in which they are incorporated exhibits a desired resultant color, e.g., a substantially neutral color such as shades of gray or brown, when activated with unfiltered sunlight, i.e., as near a neutral color as possible given the colors of the activated photochromic compounds. The relative amounts of the aforesaid photochromic compounds used will vary and depend in part upon the relative intensities of the color of the activated species of such compounds, and the ultimate color desired. Generally, the weight ratio of the aforedescribed organic photochromic compound combinations, i.e., (first to second), (first to third), and (second to third), will vary from about 1:3 to about 3:1, e.g., between about 0.75:1 and about 2:1. The combination of the first, second, and third organic photochromic compounds may have a weight ratio that will vary from about 1:3:1 to 3:1:3.

A near neutral gray color exhibits a spectrum that has relatively equal absorption in the visible range between 400 and 700 nanometers, e.g., between 440 and 660 nanometers. A near neutral brown color exhibits a spectrum in which the absorption in the 440–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used in the specification, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The photochromic compounds of the present invention may be applied to or incorporated into a host material by various methods described in the art. Such methods include dissolving or dispersing the compound within the host material, e.g., imbibition of the photochromic compound into the host material by immersion of the host material in a hot solution of the photochromic compound or by thermal transfer; providing the photochromic compound as a separate layer between adjacent layers of the host material, e.g., as a part of a polymeric film; and applying the photochromic compound as part of a coating placed on the surface of the host material. The term "imbibition" or "imbibe" is intended to mean and include permeation of the photochromic substance alone into the host material, solvent assisted transfer, absorption of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substance, e.g., to achieve a more neutral color or absorb a particular wavelength of incident light. In another embodiment, the dye may be selected to provide a desired hue to the host matrix when the photochromic substance is in an unactivated state.

The polymeric host material will usually be transparent, but may be translucent or even opaque. The polymeric product need only be transparent to that portion of the electromagnetic spectrum which activates the photochromic substance, i.e., that wavelength of ultraviolet (UV) light that produces the open form of the substance and that portion of the visible spectrum that includes the absorption maximum wavelength of the substance in its UV activated form, i.e., the open form. Further, the resin color should not be such that it masks the color of the activated form of the photochromic substance, i.e., so the change in color is readily apparent to the observer. Preferably, the host material article is a solid transparent or optically clear material, e.g., materials suitable for optical applications, such as plano and vision correcting ophthalmic lenses, windows, automotive transparencies, e.g., windshields, aircraft transparencies, plastic sheeting, polymeric films, etc.

Examples of host materials which may be used with the photochromic substances or compositions described herein include: polymers, i.e., homopolymers and copolymers, of polyol(allyl carbonate) monomers, polymers, i.e., homopolymers and copolymers, of polyfunctional acrylate monomers, polyacrylates, poly(alkylacrylates) such as poly(methyl methacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, copoly(styrene-methyl methacrylate), copoly(styrene-acrylonitrile), polyvinylbutyral, and polymers, i.e., homopolymers and copolymers, of diallylidene pentaerythritol, particularly copolymers with polyol (allyl carbonate) monomers, e.g., diethylene glycol bis(allyl carbonate) and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate) with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl and/or acrylyl functional groups as described in U.S. Pat. No. 5,200,483; cellulose acetate, cellulose propionate, cellulose butyrate, cellulose acetate butyrate, polystyrene, and copolymers of styrene with methyl methacrylate, vinyl acetate, and acrylonitrile.

The amount of photochromic substance or composition containing same applied to or incorporated into a host material is not critical provided that a sufficient amount is used to produce a photochromic effect discernible to the human eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity. Generally, the amount of total photochromic substance incorporated into or applied to a photochromic optical host material may range from about 0.15 to about 0.35 milligrams per square centimeter of surface to which the photochromic substance(s) is incorporated or applied.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The present invention is more particularly described in the following examples which are intended as illustrative only, since numerous modifications and variations therein will be apparent to those skilled in the art.

EXAMPLE 1

Step 1

2-Bromo-6-naphthol (34.0 grams, 0.15 mole) was added to a flask containing 300 milliliters of ethanol and potassium hydroxide (10.3 grams, 0.183 mole). Allyl bromide (22.1 grams, 0.183 mole) was slowly added to the stirred solution maintained under a nitrogen atmosphere. The reaction mixture was heated to reflux (66° C.) and maintained at that temperature for 3 hours. After cooling, the excess ethanol was removed under vacuum and the resulting residue was dissolved in 300 milliliters of methylene chloride and extracted with 300 milliliters of 10 weight percent aqueous sodium hydroxide. The aqueous layer was separated and washed using three 100 milliliter portions of methylene chloride. The organic extracts were combined, dried over magnesium sulfate and the methylene chloride solvent was removed under vacuum to yield 38.0 grams of product. A nuclear magnetic resonance (NMR) spectrum showed the recovered product to have a structure consistent with 2-allyloxy-6-bromonaphthalene.

Step 2

2-Allyloxy-6-bromonaphthalene (38.0 grams, 0.14 mole) from Step 1 was added to a reaction flask, heated to 95° C. and stirred for one hour under a nitrogen atmosphere. Four drops of dodecylbenzenesulfonic acid were added and the reaction mixture was stirred 1.5 hours and maintained at 95° C. The reaction mixture was cooled and distilled at a head temperature of 160° C. under a reduced pressure of 0.5 millimeters of mercury to recover 26.0 grams of product. A nuclear magnetic resonance (NMR) spectrum showed the recovered product to have a structure consistent with 7-bromo-1,2-dihydro-2-methylnaphtho[2,1-b]furan.

Step 3

7-Bromo-1,2-dihydro-2-methylnaphtho[2,1-b]furan (9.0 grams, 0.1 mole) from Step 2 was added to a reaction flask containing 70 milliliters of anhydrous tetrahydrofuran and 2.9 grams (0.12 mole) of elemental magnesium. A catalytic amount of iodine (approximately 0.02 gram) was added and the reaction mixture was heated to reflux (66° C.). After boiling became spontaneous, the remaining 17 grams of 7-bromo-1,2-dihydro-2-methylnaphtho[2,1-b]furan was added to the reaction mixture over a period of ½ hour and the reaction mixture was refluxed for an additional hour. After cooling, the resulting Grignard solution was added over a period of 45 minutes to a reaction flask containing 12.5 milliliters of trimethylborate and 100 milliliters of tetrahydrofuran that was stirred and maintained at a temperature between −5° and −10° C. After stirring an additional 30 minutes, 9.0 grams of chilled glacial acetic acid was added to the reaction mixture. This was followed by the slow addition of a cold solution of 30 weight percent hydrogen peroxide over a period of 20 minutes to the reaction mixture maintained at a temperature below 0° C. The ice bath was removed and the reaction mixture was slowly brought up to room temperature over a 45 minute period. The reaction mixture was quenched with six 100 milliliter portions of a saturated solution of aqueous ammonium sulfate (about 43 grams per 100 grams of water) which also contained approximately 1 to 2 grams of ferrous ammonium sulfate until the rust color was no longer produced. The organic layer was separated, dried over magnesium sulfate, and the tetrahydrofuran solvent was removed under vacuum. The residue was then dissolved in 10 weight percent aqueous sodium hydroxide and washed with methylene chloride. The aqueous layer was acidified to a pH of 2 and extracted with three 100 milliliter portions of methylene chloride. The organic fractions were combined, dried over magnesium sulfate and the methylene chloride solvent was removed under vacuum to yield 8.5 grams of product. A nuclear magnetic resonance (NMR) spectrum showed the recovered product to have a structure consistent with 1,2-dihydro-7-hydroxy-2-methylnaphtho[2,1-b]furan.

Step 4

3-Methylbenzoyl chloride (10.0 grams, 0.065 mole) was added to a reaction flask containing 300 milliliters of methylene chloride and 5.6 grams of benzene (0.07 mole) and stirred. Aluminum chloride (10.4 grams, 0.078 mole) was added slowly and the reaction mixture was stirred for three hours at room temperature. The resulting yellow/orange reaction mixture was added to 200 milliliters of 5 weight percent aqueous hydrochloric acid and stirred until colorless. The organic layer was separated and the aqueous layer was washed with 100 milliliters of methylene chloride. The organic extracts were combined, dried over magnesium sulfate and the methylene chloride solvent was removed under vacuum to yield 10.2 grams of product. A nuclear magnetic resonance (NMR) spectrum showed the recovered product to have a structure consistent with 3-methylbenzophenone.

Step 5

3-Methylbenzophenone (10.2 grams, 0.05 mole) from step 4 was added to a reaction flask containing 300 milliliters of tetrahydrofuran saturated with acetylene and stirred. 17.5 grams of a 18 weight percent suspension of sodium acetylide in xylene/mineral oil (0.062 mole of sodium acetylide) was added slowly to the stirred solution. After 16 hours of stirring at room temperature under a nitrogen atmosphere, the reaction mixture was quenched in 200 milliliters of 5 weight percent aqueous hydrochloric acid. The resulting mixture was stirred 10 minutes and the organic layer was removed. The aqueous layer was washed with two 100 milliliter portions of methylene chloride. The organic extracts were combined and dried over magnesium sulfate. The solvent, a mixture of tetrahydrofuran and methylene chloride, was removed under vacuum to yield 9.0 grams of product. A nuclear magnetic resonance (NMR) spectrum showed the recovered product to have a structure consistent with 1-(3-methylphenyl)-1-phenyl-2-propyn-1-ol.

Step 6

1-(3-Methylphenyl)-1-phenyl-2-propyn-1-ol (3.0 grams, 0.025 mole) from Step 5 was added to a reaction flask containing 300 milliliters of toluene and 2.7 grams (0.014 mole) of 1,2-dihydro-7-hydroxy-2-methylnaphtho[2,1-b]furan from Step 3 and stirred. A catalytic amount, an amount sufficient to produce a persistent deep red color, of dodecylbenzenesulfonic acid was added to the stirred solution and the reaction mixture was heated between 30° and 40° C. for 4 hours. The resulting reaction mixture was quenched in approximately 200 milliliters of 5 weight percent sodium hydroxide. After stirring for 5 minutes, the organic layer was separated from the quenched reaction mixture. The aqueous layer was washed with two 100 milliliter portions of methylene chloride. The organic extracts were combined, dried over magnesium sulfate and the methylene chloride and toluene solvents were removed under vacuum. The residue was chromatographed on a silica gel column using a 50:50 mixture of ethyl acetate and hexane as the eluant. The photochromic fractions were collected and the solvent was removed under vacuum to yield 0.3 gram of the desired product. A nuclear magnetic resonance (NMR) spectrum showed the recovered product to have a structure consistent with 7-(phenyl)-7-(3-methylphenyl)-7H-2-methyl-2,3-dihydrofuro[3',2',:5,6]naphtho[2,1-b]pyran.

EXAMPLE 2

The process of Example 1 was follow except for the following: in Step 6, 1,1-diphenyl-2-propyn-1-ol was used in place of 1-(3-methylphenyl)-1-phenyl-2-propyn-1-ol. The recovered product, about 0.8 gram, had a melting point of 203° to 205° C. A nuclear magnetic resonance (NMR) spectrum showed the recovered product to have a structure consistent with 7,7-diphenyl-7H-2-methyl-2,3-dihydrofuro[3',2',:5,6]naphtho[2,1-b]pyran.

EXAMPLE 3

The process of Example 1 was followed except for the following: in Step 4, 3-trifluoromethylbenzoyl chloride was used in place of 3-methylbenzoyl chloride to yield 3trifluorobenzophenone; in Step 5, 3-trifluorobenzophenone was used in place of 3-methylbenzophenone to produce 1-(3-trifluorophenyl)-1-phenyl-2-propyn-1-ol; and in Step 6, 1-(3-trifluorophenyl)-1-phenyl-2-propyn-1-ol was used in place of 1-(3-methylphenyl)-1-phenyl-2-propyn-1-ol. The recovered product, about 1 gram, had a melting point of 151° to 154° C. A nuclear magnetic resonance (NMR) spectrum showed the recovered product to have a structure consistent with 7-(phenyl)-7-(3-trifluoromethylphenyl)-7H-2-methyl-2,3-dihydrofuro[3',2',:5,6]naphtho[2,1-b]pyran.

EXAMPLE 4

The process of Example 1 was followed except for the following: in Step 4, 3-fluorobenzoyl chloride was used in place of 3-methylbenzoyl chloride to yield 3-fluorobenzophenone; in Step 5, 3-fluorobenzophenone was used in place of 3-methylbenzophenone to produce 1-(3-fluorophenyl)-1-phenyl-2-propyn-1-ol; and in Step 6, 1-(3-fluorophenyl)-1-phenyl-2-propyn-1-ol was used in place of 1 -(3-methylphenyl)-1-phenyl-2-propyn-1-ol. The recovered product, about 3.2 grams, had a melting point of 186° to 188° C. A nuclear magnetic resonance (NMR) spectrum showed the recovered product to have a structure consistent with 7-(phenyl)-7-(3-fluorophenyl)-7H-2-methyl-2,3-dihydrofuro[3',2',:5,6]naphtho[2,1-b]pyran.

EXAMPLE 5

The process of Example 1 was followed except for the following: in Step 4, 3-methoxybenzoyl chloride was used in place of 3-methylbenzoyl chloride to yield 3-methoxybenzophenone; in Step 5, 3-methoxybenzophenone was used in place of 3-methylbenzophenone to produce 1-(3-methoxyphenyl)- 1-phenyl-2-propyn-1-ol; and in Step 6, 1-(3-methoxyphenyl)-1-phenyl-2-propyn-1-ol was used in place of 1-(3-methylphenyl)- 1-phenyl-2-propyn-1-ol. The recovered product, about 2.0 grams, had a melting point of 127° to 133° C. A nuclear magnetic resonance (NMR) spectrum showed the recovered product to have a structure consistent with 7 -(phenyl)-7-(3-methoxyphenyl)-7H-2-methyl-2,3-dihydrofuro[3',2',:5,6]naphtho[2,1-b]pyran.

EXAMPLE 6

The process of Example 1 was followed except for the following: in Step 4, 2-fluorobenzoyl chloride was used in place of 3-methylbenzoyl chloride and reacted with anisole in place of benzene to yield 2-fluoro-4'-methoxybenzophenone; in Step 5, 2-fluoro-4'-methoxybenzophenone was used in place of 3-methylbenzophenone to produce 1-(2-fluorophenyl)-1-(4-methoxyphenyl)-2-propyn-1-ol; and in Step 6, 1-(2-fluorophenyl)-1-(4-methoxyphenyl)-2-propyn-1-ol was used in place of 1-(3-methylphenyl)-1-phenyl-2-propyn-1-ol. The recovered product, about 4.0 grams, had a melting point of 144° to 146° C. A nuclear magnetic resonance (NMR) spectrum showed the recovered product to have a structure consistent with 7-(2-fluorophenyl)-7-(4-methoxyphenyl)-7H-2-methyl-2,3-dihydrofuro[3',2',:5,6]naphtho[2,1-b]pyran.

EXAMPLE 7

Step 1

6-Bromo-2-naphthol (22.3 grams, 0.1 mole) was added to a reaction flask containing 200 milliliters of reagent grade acetone and a slight molar excess of chloroacetone and powdered anhydrous potassium carbonate and stirred. The stirred mixture was refluxed under nitrogen for about 16 hours, cooled to room temperature, and the acetone solvent was removed under vacuum. Water (100 milliliters) and methylene chloride (100 milliliters) were added to the resulting residue in a separatory funnel. The methylene chloride layer was separated and first washed with 5 percent aqueous sodium hydroxide to remove residual starting material and then with water. The resulting methylene chloride layer was stripped of solvent to yield 20 grams of a solid product. A nuclear magnetic resonance (NMR) spectrum showed the recovered product to have a structure consistent with 2-acetonyloxy-6-bromonaphthalene.

Step 2

2-Acetonyloxy-6-bromonaphthalene, 20 grams from Step 1, was added slowly to a reaction flask containing concentrated sulfuric acid (100 milliliters) while the acid solution was stirred and maintained at about 0° C. The resulting dark solution was stirred an additional 10 minutes and then it was poured into 500 milliliters of crushed ice. After the ice melted, the resulting residue was recovered by filtration. The residue was extracted with three 100 milliliter portions of hexane heated to about 60° C. The hexane was removed under vacuum to yield 10 grams of product. A nuclear magnetic resonance (NMR) spectrum showed the recovered product to have a structure consistent with 7-bromo-1-methylnaphtho[2,1-b]furan.

Step 3

7-Bromo-1-methylnaphtho[2,1-b]furan, 10 grams from Step 2, was placed in an autoclave with 15 grams of potassium hydroxide, 150 milliliters of water, 30 grams of poly(ethylene glycol) methyl ether (average molecular weight of 350), copper bronze (0.5 gram), and copper powder (0.5 gram). The autoclave was maintained at 200° C. for three hours while the reaction mixture was stirred at 1200 revolutions per minute. After cooling to room temperature, the reaction mixture was filtered. The filtrate was acidified with concentrated hydrochloric acid yielding a pasty solid. The paste was redissolved in 5 weight percent aqueous sodium hydroxide and again recovered by acidification and filtration. The paste was dried yielding 5.0 grams of a tan powdery product. A nuclear magnetic resonance (NMR) spectrum showed the recovered product to have a structure consistent with 7-hydroxy-1-methylnaphtho[2,1-b]furan.

Step 4

The process of Step 6 of Example 1 was followed except that 1,1-diphenyl-2-propyn-1-ol was used in place of 1-(3-methylphenyl)-1-phenyl-2-propyn-1-ol, and 7-hydroxy-1-methylnaphtho[2,1-b]furan (2.0 grams) was used in place of 1,2-dihydro-7-hydroxy-2-methylnaphtho[2,1-b]furan. The recovered product, about 0.35 gram, had a melting point of 216° to 218° C. A nuclear magnetic resonance (NMR) spectrum showed the recovered product to have a structure consistent with 7,7-diphenyl-7H-3-methylfuro[3',2',:5,6]naphtho[2,1-b]pyran.

EXAMPLE 8

Step 1

6-Bromo-2-naphthol (22.3 grams, 0.1 mole) was added to a reaction flask containing 200 milliliters of methanol and potassium hydroxide (5.6 grams, 0.1 mole). 1-Bromo-3-chloropropane (15.7 grams, 0.1 mole) was added and the mixture was refluxed for 20 hours. The methanol was removed on a rotary evaporator and 100 milliliters of 5 weight percent aqueous sodium hydroxide was added. The amount of product recovered by vacuum filtration was 20 grams. A nuclear magnetic resonance (NMR) spectrum showed the recovered product to have a structure consistent with 2-(3-chloro-1-propyloxy)-6-bromonaphthalene.

Step 2

2-(3-Chloro-1-propyloxy)-6-bromonaphthalene, 20 grams from Step 1, was added to a reaction flask containing 150 milliliters of benzene. Aluminum chloride (14 grams) was added to the reaction flask and the reaction mixture was stirred and heated slowly to the reflux temperature. At the reflux temperature, a large amount of hydrogen chloride evolved. After the evolution of hydrogen chloride tapered off, the reaction mixture was cooled and poured into a large volume of ice and water. The organic layer was separated and washed with water. The benzene solvent was removed under vacuum. The resultant oil was chromatographed on a silica column using a 3:1 mixture of hexane:chloroform as the eluant. The product (5 grams) was recovered in the form of a clear oil. A nuclear magnetic resonance (NMR) spectrum showed the recovered product to have a structure consistent with 8-bromo-1,2-dihydro-3H-naphtho[2,1-b]pyran.

Step 3

8-bromo-1,2-dihydro-3H-naphtho[2,1-b]pyran, 5.0 grams from Step 2, was placed in an autoclave with 15 grams of potassium hydroxide, 150 milliliters of water, 30 grams of poly(ethylene glycol) methyl ether (average molecular weight of 350), copper bronze (0.5 gram), and copper powder (0.5 gram). The autoclave was maintained at 200° C. for four hours while the reaction mixture was stirred at 1200 revolutions per minute. After the autoclave was cooled to room temperature, 50 milliliters of methylene chloride was added and the reaction mixture was filtered. The aqueous layer was separated and acidified with concentrated hydrochloric acid. The solid that precipitated was suction filtered and dried yielding 2 grams of the desired product, 1,2-dihydro-8-hydroxy-3H-naphtho[2,1-b]pyran.

Step 4

The process of Step 6 of Example 1 was followed except that 1,1-diphenyl-2-propyn-1-ol was used in place of 1-(3-methylphenyl)-1-phenyl-2-propyn-1-ol and 1,2-dihydro-8-hydroxy-3H-naphtho[2,1-b]pyran (2.0 grams) was used in place of 1,2-dihydro-7-hydroxy-2-methylnaphtho[2,1-b]furan. The recovered product (0.7 gram) had a melting point of 248° to 249° C. A nuclear magnetic resonance (NMR) spectrum showed the recovered product to have a structure consistent with 9,9-diphenyl-3H,9H-1,2-dihydronaphtho[2,1-b:6,5-b']dipyran.

EXAMPLES 9 AND 10

Step 1

2,6-Dihydroxynaphthalene (20.0 grams, 0.125 mole) was added to a reaction flask containing 20.0 grams (0.153 mole) of ethylacetoacetate and the mixture was cooled to 0° C. Sulfuric acid (200 milliliters of an 80 weight percent aqueous solution) was added slowly with stirring to the reaction mixture over a period of about 30 minutes. Under a blanket of nitrogen, the reaction was first stirred at 0° C. for 3 hours and then at room temperature for an additional 24 hours. The reaction was quenched in ice water at which time a precipitate formed. The recovered precipitate was dissolved in aqueous sodium bicarbonate. The pH of the solution was adjusted to 6 and the precipitate was collected by vacuum filtration. The resulting product was washed with 95 percent aqueous ethanol and dried to yield 7.0 grams of a 50:50 mixture of 8-hydroxy-1-methyl-3H-naphtho[2,1-b]pyran-3-one and 8-hydroxy-3-methyl-1H-naphtho[2,1-b]pyran-1-one.

Step 2

The 50:50 mixture of reaction products (3.0 grams) from Step 1 was added to a reaction flask containing 200 milliliters of toluene and 3.9 grams of 1-(2,4-dimethoxyphenyl)-1-(4'-methoxyphenyl)-2-propyn-1-ol and stirred. A catalytic amount, an amount sufficient to produce a persistent deep red color, of p-toluenesulfonic acid was added to the stirred solution. The reaction was quenched after 48 hours in a saturated sodium chloride solution. The organic layer was separated and dried with magnesium sulfate and the toluene solvent was removed under vacuum. The resulting residue was chromatographed twice on a silica gel column, first, using chloroform as the eluant and then a 50:50 mixture of ethyl acetate and hexane. The recovered products were separately collected and crystallized using a ether:hexane mixture. The first recovered product (0.35 gram) had a melting point of 205° to 207° C. and the second recovered product (0.56 gram) had a melting point of 135° to 138° C. Nuclear magnetic resonance (NMR) spectra showed the first recovered product to have a structure consistent with 9-(2,4-dimethoxyphenyl)-9-(4'-methoxyphenyl)-1-methyl-3H,9H-naphtho[2,1-b:6,5-b']dipyran-3-one (Compound Example 9) and the second recovered product to have a structure consistent with 9-(2,4-dimethoxyphenyl)-9-(4'-methoxyphenyl)-3-methyl-1H,9H-naphtho[2,1-b:6,5-b']dipyran-1-one (Compound Example 10).

COMPARATIVE EXAMPLE 1

1,1-diphenyl-2-propyn-1-ol (20.8 grams, 0.1 mole) was added to a reaction flask containing 200 milliliters of benzene and 15 grams of 2-naphthol. The reaction mixture was warmed to 55° C. and after all of the 2-naphthol was dissolved, 0.25 gram of p-toluenesulfonic acid was added. The mixture changed from light tan to dark black in color and the temperature rose to 70° C. After a few minutes, the reaction mixture became lighter in color and began to cool. Thirty minutes later, the contents of the flask were poured into 100 milliliters of 10 percent aqueous sodium hydroxide and shaken. The organic layer was separated, washed once with 10 percent aqueous sodium hydroxide, and then washed with water. The benzene solvent was removed on a rotary evaporator and the resulting light tan residue was slurried with 100 milliliters of hexane and then filtered. The filtered solid was washed again with 100 milliliters of hexane and dried to provide 18.4 grams of the product, 3,3-diphenyl-3H-naphtho[2,1-b]pyran. The solid product had a melting point of 156° to 158° C. and was 98 percent pure as determined by liquid chromatographic analysis.

COMPARATIVE EXAMPLE 2

Step 1

A reaction flask was charged with 200 milliliters of acetone, powdered potassium carbonate (13.8 grams, 0.1 mole) and 2,6-dihydroxynaphthalene (16.0 grams, 0.1 mole). Dimethylsulfate (12.6 grams, 0.1 mole) was added dropwise and the reaction mixture was stirred at room temperature for 72 hours under a nitrogen atmosphere. Sodium hydroxide (200 milliliters of a 10 weight percent aqueous solution) was added to the reaction flask. The white precipitate that formed was removed by vacuum filtration. The aqueous filtrate was acidified with hydrochloric acid to a pH of 3 and the aqueous solution extracted three times with 100 milliliter portions of methylene chloride. The extracts were combined and dried over anhydrous magnesium sulfate for 10 minutes. The solvent, a mixture of methylene chloride and acetone, was removed under vacuum. The residue was washed with hot water and dried to yield 3.0 grams of a solid product. A nuclear magnetic resonance (NMR) spectrum showed the product to have a structure consistent with 6-methoxy-2-hydroxynaphthalene.

Step 2

6-Methoxy-2-hydroxynaphthalene (1.1 grams, 0.006 mole) from Step 1, was added to a reaction flask containing 100 milliliters of benzene and 1,1-diphenyl-2-propyn-1-ol (1.3 grams, 0.006 mole). A catalytic amount (approximately 20.0 milligrams) of p-toluenesulfonic acid was added and the resulting mixture was stirred under a nitrogen atmosphere. The reaction mixture was heated at 50° C. for 4 hours, cooled, and then 200 milliliters of a 10 weight percent aqueous sodium hydroxide solution was added. After stirring for 15 minutes, the reaction mixture was extracted twice with 100 milliliter portions of methylene chloride. The extracts were combined, dried over anhydrous magnesium sulfate and the solvent, a mixture of benzene and methylene chloride, was removed under vacuum. The product (1.0 gram) melted at 173° to 175° C. A nuclear magnetic resonance (NMR) spectrum showed the product to have a structure consistent with 3,3-diphenyl-8-methoxy-3H-naphtho[2,1-b]pyran.

EXAMPLE 11

Part A

The compounds of the Examples and the Comparative Examples were dissolved in diethylene glycol dimethyl ether. The concentrations of the resulting solutions were approximately 0.5 milligram per milliliter. Each solution was tested in a UV spectrophotometer to determine the lambda max (UV). The lambda max (UV) reported in Table 1 for each of the Examples is the wavelength in the ultraviolet range closest to the visible spectrum.

Part B

Testing was done with selected photochromic naphthopyrans imbibed into test square polymerizates by a thermal transfer process. The test square polymerizates were prepared from a homopolymer of diethylene glycol bis(allyl carbonate) and measured ⅛ inch (0.3 centimeters)×2 inches (5.1 centimeters)×2 inches (5.1 centimeters). The test squares were imbibed by the following procedure. Each naphthopyran was dissolved into toluene to form a 4 weight percent solution of the compound. A piece of No.4 Whatman filter paper was saturated with the naphthopyran toluene solution and allowed to air dry. The dried filter paper was placed on one side of the test square. A piece of untreated filter paper was placed on the other side of the polymeric test square and the resulting sandwich was placed between two flat aluminum metal plates. The entire assembly was then placed in an oven kept at 135° to 155° C. for a time sufficient to thermally transfer the naphthopyran into the polymeric test square. After cooling, each test square was washed with acetone. The residence time in the oven for the test squares was adjusted to imbibe comparable amounts of the naphthopyran compounds. This was done in order to yield a comparable UV absorbance at the activating wavelength of the compound.

Part C

The photochromic test squares of Part B were tested for photochromic response rates on an optical bench. Prior to testing on the optical bench, the photochromic test squares were exposed to 365 nanometer ultraviolet light for about 15 minutes to activate the photochromic compounds and then placed into a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 75° F. (23.9° C.).

The optical bench comprises a 150 watt Xenon arc lamp, a tungsten lamp, power supplies for both lamps, condensing lenses as needed to maintain collimated light beams from both lamps, a remote controlled shutter, a copper sulfate bath acting as a heat sink for the arc lamp, a Schott WG-320 nm cut-off filter which removes short wavelength radiation, neutral density filter(s), a sample holder in which the sample to be tested is inserted, a photopic filter, light detector, and radiometer assembly, a strip chart recorder, and a means for maintaining the alignment of the aforestated components during testing.

Change in optical density (ΔOD) of a sample was determined by inserting a photochromic test sample in the bleached state into the sample holder, adjusting the transmittance scale to 100%, opening the shutter from the Xenon lamp to provide ultraviolet radiation to change the sample from the bleached state to an activated (darkened) state, measuring the transmittance through the sample. The transmittance was measured by directing a beam of light from the tungsten lamp at a small angle normal to the surface of the sample, through the sample, and to a photopic filter, light detector and radiometer assembly. The photopic filter passes wavelengths such that the detector mimics the response of the human eye and produces output signals that are processed by the radiometer. The change in optical density was calculated according to the formula $\Delta OD = \log(100/\% T_a)$ where % $T_a$ is the percent transmittance in the activated state and the logarithm is to the base 10.

The ΔOD/Min, which represents the sensitivity of the photochromic compound's response to UV light, was measured over the first five (5) seconds of UV exposure, then expressed on a per minute basis. The saturation optical density (OD) was taken under identical conditions as the ΔOD/Min, except UV exposure was continued for 20 minutes. The lambda max (VIS) reported in Table 2 is the wavelength in the visible spectrum at which the maximum absorption of the activated (colored) form of the photochromic compound in a homopolymer of diethylene glycol bis(allyl carbonate) occurs. The bleach rate (T½) is the time interval in seconds for the absorbance of the activated form of the naphthopyran in the test squares to reach one half the highest absorbance at room temperature (75° F., 23.9° C.) after removal of the source of activating light. Results for the compounds of the Examples are tabulated in Table 2.

TABLE 1

| COMPOUND EXAMPLES | Lambda max (UV) |
| --- | --- |
| 1 | 394 |
| 2 | 394 |
| 3 | 396 |
| 4 | 394 |
| 5 | 395 |
| 6 | 393 |
| 7 | 372 |
| 8 | 382 |
| 9 | 396 |
| 10 | 384 |
| COMPARATIVE EXAMPLES | |
| 1 | 359 |
| 2 | 376 |

TABLE 2

| | LAMBDA MAX (VIS) | Δ OD/Min SENSITIVITY | OD @ SATURATION | BLEACH RATE T½ (SEC.) |
| --- | --- | --- | --- | --- |
| COMPOUND EXAMPLE | | | | |
| 2 | 488 nm | 1.35 | 0.66 | 106 |
| 3 | 494 nm | 1.38 | 0.74 | 131 |
| 4 | 489 nm | 1.44 | 0.76 | 109 |
| 5 | 495 nm | 1.43 | 0.74 | 165 |
| COMPARATIVE EXAMPLES | | | | |
| 1 | 430 nm | 0.87 | 0.36 | 45 |
| 2 | 473 nm | 1.25 | 0.73 | 87 |

The results of Table 1 demonstrate the unexpectedly higher lambda max (UV) wavelengths of the compounds of the present invention, vis-a-vis, Comparative Example 1, which has no substituents on the naphthalene nucleus, and Comparative Example 2, which has a methoxy substituent at the number 8 carbon atom. Table 2 shows that each of the tested compounds of the present invention have unexpectedly higher lambda max (VIS) wavelengths, increased sensitivity, longer bleach rate values, and comparable saturation optical density results as compared to the Comparative Examples.

The present invention has been described with reference to specific details of certain embodiments thereof, it is not intended that such details should be regarded as limitations upon the scope of the invention except insofar as they are included in the accompanying claims.

What is claimed is:

1. A naphthopyran compound represented by one of the following graphic formulae:

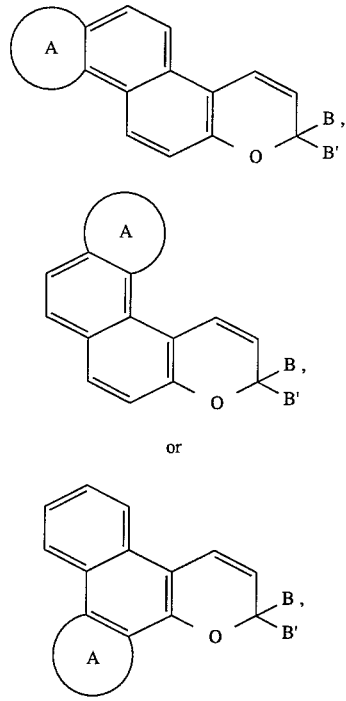

wherein, (a) A is a heterocyclic ring that may be represented by one of the following graphic formulae:

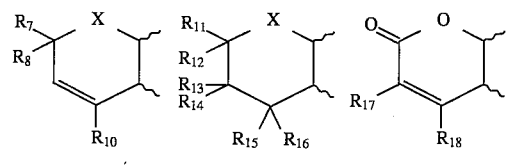

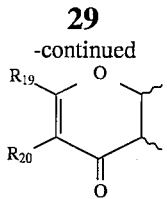

wherein X is an oxygen or a nitrogen atom, said nitrogen atom being substituted with a hydrogen or $C_1$–$C_4$ alkyl; $R_7$, $R_8$ and $R_{10}$ are each hydrogen, $C_1$–$C_6$ alkyl or phenyl, provided that when $R_7$ is phenyl, $R_8$ is hydrogen or $C_1$–$C_6$ alkyl and when $R_8$ is phenyl, $R_7$ is hydrogen or $C_1$–$C_6$ alkyl; $R_{11}$, $R_{12}$, $R_{13}$, $R_{14}$, $R_{15}$ and $R_{16}$ are each hydrogen, $C_1$–$C_6$ alkyl, $C_1$–$C_6$ alkoxy or phenyl; $R_{17}$ is hydrogen, $C_1$–$C_6$ alkyl, substituted or unsubstituted phenyl or halogen; $R_{18}$ is hydrogen, $C_1$–$C_6$ alkyl, phenyl, carboxy, $C_1$–$C_6$ alkoxycarbonyl or $C_1$–$C_6$ haloalkoxycarbonyl; $R_{19}$ and $R_{20}$ are each hydrogen, $C_1$–$C_6$ alkyl or phenyl; said phenyl substituents being $C_1$–$C_5$ alkyl; and said halogen or (halo) groups being chloro or bromo; and (b) B and B' are each selected from the group consisting of the substituted or unsubstituted aryl groups phenyl and naphthyl, said aryl substituents being selected from the group consisting of hydroxy, $C_1$–$C_5$ alkyl, $C_1$–$C_5$ haloalkyl, $C_1$–$C_5$ alkoxy, $C_1$–$C_5$ alkoxy($C_1$–$C_4$)alkyl, $C_1$–$C_5$ dialkylamino, acryloxy, methacryloxy and halogen, said halogen or (halo) groups being fluoro, chloro, or bromo.

2. The naphthopyran of claim 1 wherein:

(a) heterocyclic ring A is fused to the i side of said naphthopyran, X is an oxygen atom; $R_7$, $R_8$ and $R_{10}$ are each hydrogen, $C_1$–$C_3$ alkyl or phenyl, provided that when $R_7$ is phenyl, $R_8$ is hydrogen or $C_1$–$C_3$ alkyl and when $R_8$ is phenyl, $R_7$ is hydrogen or $C_1$–$C_3$ alkyl; $R_{11}$, $R_{12}$, $R_{13}$, $R_{14}$, $R_{15}$ and $R_{16}$ are each hydrogen, $C_1$–$C_3$ alkyl, $C_1$–$C_3$ alkoxy or phenyl; $R_{17}$ is hydrogen, $C_1$–$C_3$ alkyl, substituted or unsubstituted phenyl or halogen; $R_{18}$ is hydrogen, $C_1$–$C_3$ alkyl, phenyl, carboxy, $C_1$–$C_3$ alkoxycarbonyl or $C_1$–$C_3$ haloalkoxycarbonyl; $R_{19}$ and $R_{20}$ are each hydrogen, $C_1$–$C_3$ alkyl or phenyl; said phenyl substituents being $C_1$–$C_3$ alkyl; and said halogen or (halo) groups being chloro or bromo; and (b) B and B' are represented respectively by the following graphic formulae:

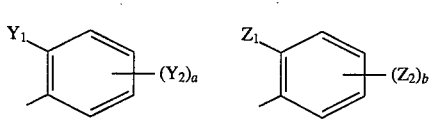

wherein $Y_1$ and $Z_1$ are each hydrogen, $C_1$–$C_5$ alkyl, $C_1$–$C_5$ alkoxy, fluoro or chloro and $Y_2$ and $Z_2$ are each $C_1$–$C_5$ alkyl, $C_1$–$C_5$ alkoxy, hydroxy, fluoro, chloro, acryloxy or methacryloxy, and a and b are each integers of from 0 to 2.

3. The naphthopyran of claim 2 wherein $R_{11}$, $R_{12}$, $R_{13}$, $R_{14}$, $R_{15}$ and $R_{16}$ are each hydrogen, methyl or methoxy, $R_{17}$ is hydrogen, methyl or chloro, $R_{18}$, $R_{19}$ and $R_{20}$ are each hydrogen or methyl, $Y_1$ and $Z_1$ are each hydrogen, $C_1$–$C_3$ alkyl, $C_1$–$C_3$ alkoxy or fluoro, $Y_2$ and $Z_2$ are each $C_1$–$C_3$ alkyl or $C_1$–$C_3$ alkoxy, a is the integer 0 or 1, and b is an integer from 0 to 2.

4. A naphthopyran selected from the group consisting of:

(a) 9,9-diphenyl-3H-9H-1,2-dihydronaphtho[2,1-b:6,5-b']dipyran;

(b) 9-(2,4-dimethoxyphenyl)-9-(4'-methoxyphenyl)-1-methyl-3H,9H-naphtho[2,1-b:6,5-b']dipyran-3-one; and (c) 9-(2,4-dimethoxyphenyl)-9-(4'-methoxyphenyl)-3-methyl-1H,9H-naphtho[2,1-b:6,5-b]dipyran-1-one.

5. A photochromic article comprising an organic host material and a photochromic amount of a photochromic naphthopyran compound of claim 1.

6. The photochromic article of claim 5 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyurethane, poly(ethylene terephthalate), polystyrene, copoly(styrene-methylmethacrylate), copoly(styrene-acrylonitrile), polyvinylbutyral, and polymers of members selected from the group consisting of polyol(allyl carbonate) monomers, polyfunctional acrylate monomers, and diallylidene pentaerythritol monomers.

7. The photochromic article of claim 6, where the napthopyran compound is represented by the following graphic formula:

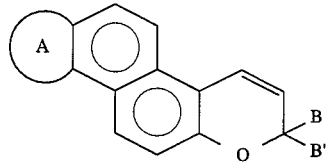

wherein A is a heterocyclic ring that may be represented by one of the following graphic formulae:

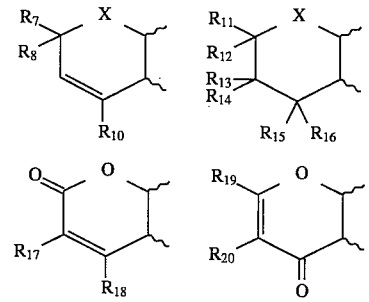

wherein X is oxygen; $R_7$, $R_8$ and $R_{10}$ are each hydrogen, $C_1$–$C_3$ alkyl or phenyl, provided that when $R_7$ is phenyl, $R_8$ is hydrogen or $C_1$–$C_3$ alkyl and when $R_8$ is phenyl, $R_7$ is hydrogen or $C_1$–$C_3$ alkyl; $R_{11}$, $R_{12}$, $R_{13}$, $R_{14}$, $R_{15}$ and $R_{16}$ are each hydrogen, $C_1$–$C_3$ alkyl, $C_1$–$C_3$ alkoxy or phenyl; $R_{17}$ is hydrogen, $C_1$–$C_3$ alkyl, substituted or unsubstituted phenyl or halogen; $R_{18}$ is hydrogen, $C_1$–$C_3$ alkyl, phenyl, carboxy, $C_1$–$C_3$ alkoxycarbonyl or $C_1$–$C_3$ haloalkoxycarbonyl; $R_{19}$ and $R_{20}$ are each hydrogen, $C_1$–$C_3$ alkyl or phenyl; said phenyl substituents being $C_1$–$C_3$ alkyl; and said halogen or (halo) groups being chloro or bromo; and wherein B and B' are represented respectively by the following graphic formulae:

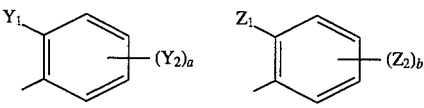

wherein $Y_1$ and $Z_1$ are each hydrogen, $C_1$–$C_5$ alkyl, $C_1$–$C_5$ alkoxy, fluoro or chloro, and $Y_2$ and $Z_2$ are each $C_1$–$C_5$ alkyl, $C_1$–$C_5$ alkoxy, hydroxy, fluoro, chloro, acryloxy or methacryloxy, and a and b are each integers of from 0 to 2.

8. The photochromic article of claim 7, wherein $R_{11}$, $R_{12}$, $R_{13}$, $R_{14}$, $R_{15}$ and $R_{16}$ are each hydrogen, methyl or methoxy, $R_{17}$ is hydrogen, methyl or chloro, $R_{18}$, $R_{19}$ and $R_{20}$ are each hydrogen or methyl, $Y_1$ and $Z_1$ are each hydrogen, $C_1$–$C_3$ alkyl, $C_1$–$C_3$ alkoxy or fluoro, $Y_2$ and $Z_2$ are each $C_1$–$C_3$ alkyl or $C_1$–$C_3$ alkoxy, a is the integer 0 or 1, and b is an integer from 0 to 2.

9. The photochromic article of claim 8 wherein the organic host material is a solid transparent homopolymer or copolymer of diethylene glycol bis(allyl carbonate), thermoplastic polycarbonate, cellulose acetate butyrate, poly(methylmethacrylate), polyvinylbutyral, or a polyurethane.

10. The photochromic article of claim 9 wherein the photochromic naphthopyran compound is present in an amount of from about 0.15 to 0.35 milligrams per square centimeter of organic host material surface to which the photochromic substance(s) is incorporated or applied.

11. The photochromic article of claim 10 wherein the article is a lens.

12. A photochromic article comprising, in combination, a solid transparent polymerized organic host material and a photochromic amount of (a) at least one organic photochromic compound having at least one activated absorption maxima within the visible range of between about 400 to 700 nanometers associated with said host material, and (b) at least one photochromic naphthopyran compound of claim 1.

13. The photochromic article of claim 12 wherein the organic host material is selected from the group consisting of polyacrylates, cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonate, polyurethane, poly(ethylene terephthalate), polystyrene, copoly(styrene-methylmethacrylate), copoly(styrene-acrylonitrile, polyvinylbutyral, and polymers of members selected from the group consisting of polyol(allyl carbonate) monomers, polyfunctional acrylate monomers, and diallylidene pentaerythritol monomers.

14. The photochromic article of claim 13 wherein the photochromic naphthopyran compound (b) is represented by the following graphic formula:

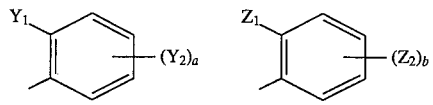

wherein A is a heterocyclic ring that may be represented by one of the following graphic formulae:

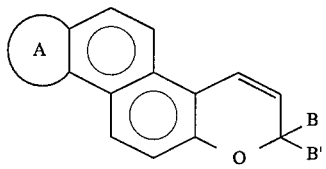

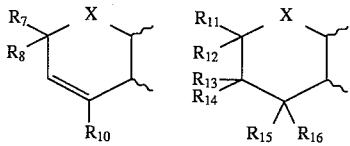

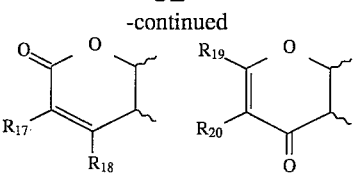

wherein X is oxygen; $R_7$, $R_8$ and $R_{10}$ are each hydrogen, $C_1$–$C_3$ alkyl or phenyl, provided that when $R_7$ is phenyl, $R_8$ is hydrogen or $C_1$–$C_3$ alkyl and when $R_8$ is phenyl, $R_7$ is hydrogen or $C_1$–$C_3$ alkyl; $R_{11}$, $R_{12}$, $R_{13}$, $R_{14}$, $R_{15}$ and $R_{16}$ are each hydrogen, $C_1$–$C_3$ alkyl, $C_1$–$C_3$ alkoxy or phenyl; $R_{17}$ is hydrogen, $C_1$–$C_3$ alkyl, substituted or unsubstituted phenyl or halogen; $R_{18}$ is hydrogen, $C_1$–$C_3$ alkyl, phenyl, carboxy, $C_1$–$C_3$ alkoxycarbonyl or $C_1$–$C_3$ haloalkoxycarbonyl; $R_{19}$ and $R_{20}$ are each hydrogen, $C_1$–$C_3$ alkyl or phenyl; said phenyl substituents being $C_1$–$C_3$ alkyl; and said halogen or (halo) groups being chloro or bromo; and wherein B and B' are represented respectively by the following graphic formulae:

wherein $Y_1$ and $Z_1$ are each hydrogen, $C_1$–$C_5$ alkyl, $C_1$–$C_5$ alkoxy, fluoro or chloro, and $Y_2$ and $Z_2$ are each $C_1$–$C_5$ alkyl, $C_1$–$C_5$ alkoxy, hydroxy, fluoro, chloro, acryloxy or methacryloxy, and a and b are each integers of from 0 to 2.

15. The photochromic article of claim 14 wherein the organic host material is a solid transparent homopolymer or copolymer of diethylene glycol bis(allyl carbonate), thermoplastic polycarbonate, cellulose acetate butyrate, poly(methylmethacrylate), polyvinylbutyral, or a polyurethane.

16. The photochromic article of claim 15 wherein the organic photochromic compound (a) is selected from the group consisting of spiro(indoline)naphthoxazines, spiro(indoline)pyridobenzoxazines, spiro(benzindoline)pyridobenzoxazines, spiro(benzindoline)naphthoxazines, spiro(benzindoline)naphthopyrans, spiro(indoline)benzoxazines, spiro(indoline)benzopyrans, spiro(indoline)naphthopyrans, spiro(indoline)quinopyrans, spiro(indoline)pyrans, 3H-naphtho[2,1-b]pyrans other than the photochromic naphthopyrans (b), 2H-naphtho[2,1-b]pyrans, and mixtures of such photochromic substances.

17. The photochromic article of claim 16 wherein each photochromic compound associated with the organic host material is present in an amount of from about 0.1 B to 0.35 milligrams per square centimeter of organic host material surface to which the photochromic compound is incorporated or applied.

18. The photochromic article of claim 17 wherein the article is an ophthalmic lens.

19. A photochromic article comprising, in combination, a solid transparent polymerized organic host material and a photochromic amount of (a) at least one organic photochromic compound represented by the graphic formula:

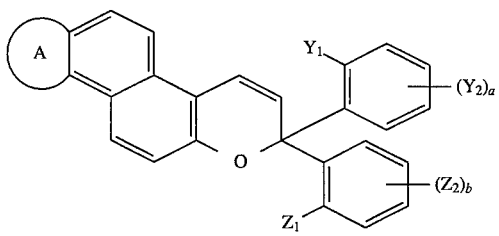

wherein, A is a heterocyclic ring represented by the following graphic formulae:

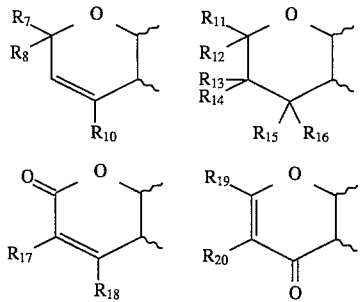

wherein $R_7$, $R_8$ and $R_{10}$ are each hydrogen, $C_1$–$C_3$ alkyl or phenyl, provided that when $R_7$ is phenyl, $R_8$ is hydrogen or $C_1$–$C_3$ alkyl and when $R_8$ is phenyl, $R_7$ is hydrogen or $C_1$–$C_3$ alkyl; $R_{11}$, $R_{12}$, $R_{13}$, $R_{14}$, $R_{15}$ and $R_{16}$ are each hydrogen, $C_1$–$C_3$ alkyl, $C_1$–$C_3$ alkoxy or phenyl; $R_{17}$ is hydrogen, $C_1$–$C_3$ alkyl, substituted or unsubstituted phenyl or halogen; $R_{18}$ is hydrogen, $C_1$–$C_3$ alkyl, phenyl, carboxy, $C_1$–$C_3$ alkoxycarbonyl or $C_1$–$C_3$ haloalkoxycarbonyl; $R_{19}$ and $R_{20}$ are each hydrogen, $C_1$–$C_3$ alkyl or phenyl; $Y_1$ and $Z_1$ are each hydrogen, $C_1$–$C_5$ alkyl, $C_1$–$C_5$ alkoxy, fluoro or chloro; $Y_2$ and $Z_2$ are each $C_1C_5$ alkyl, $C_1$–$C_5$ alkoxy, hydroxy, fluoro, chloro, acryloxy or methacryloxy; said phenyl substituents being $C_1$–$C_3$ alkyl, said halogen or (halo) groups being chloro or bromo, and a and b are each integers from 0 to 2; and (b) at least one organic photochromic compound selected from the group consisting of spiro(indoline)naphthoxazines, spiro(indoline)pyridobenzoxazines, spiro(indoline)-benzoxazines, spiro(indoline)benzopyrans, spiro(indoline)-naphthopyrans, 2H-naphtho[2,1-b]pyrans, and 3H-naphtho[2,1-b]pyrans, the weight ratio of the photochromic compounds (a):(b) being from about 1:3 to about 3:1.

20. The photochromic article of claim 19 wherein the organic host material is a solid transparent homopolymer or copolymer of diethylene glycol bis(allyl carbonate), thermoplastic polycarbonate, cellulose acetate butyrate, poly(methylmethacrylate), polyvinylbutyral, or a polyurethane.

21. The photochromic article of claim 20 wherein $R_7$, $R_8$ and $R_{10}$ are each hydrogen or methyl; $R_{11}$, $R_{12}$, $R_{13}$, $R_{14}$, $R_{15}$ and $R_{16}$ are each hydrogen, methyl or methoxy, $R_{17}$ is hydrogen, methyl or chloro; $R_{18}$, $R_{19}$ and $R_{20}$ are each hydrogen or methyl; $Y_1$ and $Z_1$ are each hydrogen, $C_1$–$C_3$ alkyl, $C_1$–$C_3$ alkoxy or fluoro; $Y_2$ and $Z_2$ are each $C_1$–$C_3$ alkyl or $C_1$–$C_3$ alkoxy, a is the integer 0 or 1, and b is an integer from 0 to 2.

22. The photochromic article of claim 21 wherein the organic photochromic compound (b) is selected from spiro(indoline)naphthoxazines or spiro(indoline)pyrido benzoxazines.

* * * * *

UNITED STATES PATENT AND TRADEMARK OFFICE
CERTIFICATE OF CORRECTION

PATENT NO. : 5,565,147
DATED : October 15, 1996
INVENTOR(S) : David B. Knowles et al It is certified that error appears in the above-indentified patent and that said Letters Patent is hereby corrected as shown below:

Column 31, claim 14, line 58,
    "that may be" should be deleted.

Column 32, claim 17, line 56, "0.1 B" should be --0.15--.

Column 34, claim 19, line 4, "$C_1C_5$" should be --$C_1$-$C_5$--.

Signed and Sealed this

Twenty-ninth Day of December, 1998

Attest:

BRUCE LEHMAN

*Attesting Officer*    *Commissioner of Patents and Trademarks*